United States Patent [19]

Beriger et al.

[11] 4,017,611

[45] Apr. 12, 1977

[54] CONTROL OF INSECTS WITH 3-HYDROXYMETHACRYLIC ACID METHYL ESTER DIMETHYLTHIONOPHOSPHATE

[75] Inventors: Ernst Beriger, Neuallschwil; Ladislaus Pinter, Basel, both of Switzerland

[73] Assignee: Ciba-Geigy AG, Basel, Switzerland

[22] Filed: Oct. 10, 1975

[21] Appl. No.: 621,454

Related U.S. Application Data

[60] Division of Ser. No. 348,426, April 5, 1973, Pat. No. 3,923,932, which is a continuation of Ser. No. 136,193, April 21, 1971, abandoned.

[30] Foreign Application Priority Data

Apr. 21, 1970 Switzerland .................... 6028/70

[52] U.S. Cl. ............................................. 424/212
[51] Int. Cl.² ........................................... A01N 9/36

[58] Field of Search ................... 424/212; 260/941

[56] References Cited

UNITED STATES PATENTS

| 2,685,552 | 8/1954 | Stiles .............................. 424/212 |
| 3,594,454 | 7/1971 | Beriger et al. ................... 260/941 |
| 3,923,932 | 12/1975 | Beriger et al. ................... 260/941 |

*Primary Examiner*—Leonard Schenkman
*Attorney, Agent, or Firm*—Frederick H. Rabin

[57] ABSTRACT

The compound of the formula

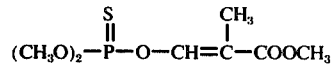

its manufacture and use in pest control.

2 Claims, No Drawings

CONTROL OF INSECTS WITH 3-HYDROXYMETHACRYLIC ACID METHYL ESTER DIMETHYLTHIONOPHOSPHATE

CROSS REFERENCE TO RELATED APPLICATIONS

This is a division of Application Ser. No. 348,426 filed Apr. 5, 1973, now U.S. Pat. No. 3,923,932 which is a continuation of Application Ser. No. 136,193 filed Apr. 21, 1971, now abandoned.

This invention relates to pest control agents.

The present invention relates to the compound of formula

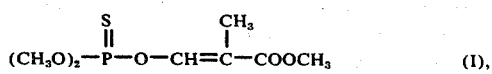

$$(CH_3O)_2-\overset{\overset{S}{\|}}{P}-O-CH=\overset{\overset{CH_3}{|}}{C}-COOCH_3 \quad (I),$$

and its manufacture and use in pest control.

The compound according to the invention of formula I is manufactured in known fashion by reacting dimethylthiochlorophosphate with the methyl ester of a α-hydroxymethylenepropionic acid, or preferably with a salt thereof, e.g. an alkali salt.

The reaction is carried out in an inert, preferably polar solvent such as dioxane, acetonitrile, dimethylsulfoxide, dimethylformamide, or for example benzene, toluene, xylene, chlorobenzene and others, at temperatures of 15° to 80° C, especially 30° to 70° C.

The compounds of formula I have a broad biocidal activity spectrum and can be used for combating various animal and vegetable pests.

They are suitable in particular for combating insect types of stored product and grain pests, since they fulfil all the necessary requirements of an insecticide for stored products, these being 1. low lethal minimum concentration for insects
2. low toxicity towards humans and domestic animals
3. an uniform action over many months
4. no residue problems
5. a faint characteristic smell.

Compared to the similarly constituted compounds of French Pat. No. 1530955, or the commercial product PHOSDRIN (Registered Trade Mark) of the formula

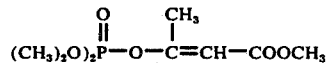

$$(CH_3)_2O)_2P-O-\overset{\overset{CH_3}{|}}{C}=CH-COOCH_3$$

warm blooded toxicity $LD_{50}$ 3–7 mg/kg body weight orally (Rats) or DDVP (dimethyldichlorvinylphosphate): warm blooded toxicity $LD_{50}$ 50 mg/kg body weight orally (Rats), the material of formula I only has a low toxicity of $LD_{50}$ 500 mg/kg orally (Rats), but also has the advantages of stronger insecticidal action, very long effective life (more than 4 months), increased vapour pressure, lack of residue problems, and a faint characteristic smell. Furthermore it diffuses easily into the gaps between stored foodstuffs.

By virtue of these properties the following typical storage pests and crop pests can be combated with the active substance of formula I:

| Latin Name | Common Name |
|---|---|
| Oryzaephilus surinamensis | Saw-toothed grain beetle |
| Trogoderma granarium | Knapra beetle |
| Lasioderma serricorne | cigarette beetle |
| Chryptolestes ferrugineus | rust-red grain beetle |
| Stegobium paniceum | biscuit beetle |
| Necrobia rufipes | Copra beetle |
| Anthrenus vorax | carpet beetle |
| Sitophilus granarium | grain weevil |
| Sitophilus oryzae | lesser rice weevil |
| Sitophilus zea mais | greater rice weevil |
| Rhizopertha dominica | lesser grain borer |
| Acanthoscelides obtectus | dried bean beetle |
| Sitotroga cerealella | Angoumois grain moth |
| Nemapagon granellus | corn moth |
| Tyrophagus putrescentiae | copra mite |
| Acarus siro | flour mite |
| Ephestia kuehniella | mediterranean flour moth |
| Araecerus fasciculatus | coffee bean weevil |
| Carpophilus hemipterus | dried fruit beetle |
| Tenebrio molitor | Yellow mealworm beetle |
| Tribolium castaneum | rust-red flour beetle |
| Tribolium destructor | dark flour beetle |
| Tribolium confusum | confused flour beetle |
| as well as cockroaches such as | |
| Blattella germanica | German cockroach |
| Periplaneta americana | American cockroach |
| Blatta orientalis | Oriental cockroach |

The active substance of formula I can be used as pure concentrate or in admixture or conjunction with suitable carriers and/or adjuvants.

Suitable carriers and adjuvants can be solid or liquid and correspond to the substances conventionally used in formulation, technique, for example natural or regenerated mineral substances, solvents, dispersants, wetting agents, adhesives, thickeners, binders or fertilisers.

The active substance of formula I can be used in pure form, for example by treating warmed containers with the agent and allowing the contents to evaporate.

The active substance can also be formulated in customary solid or liquid fashion and can be used as an emulsion concentrate, spraying powder, dusting powder, granulate or spray. Of primary use are gas phase, fumigation or sprayed applications. In this way crops such as wheat, rye, barley, oats, millet, rice, maize and other dried fruits can be treated during filling into silo storage, for example on a conveyor belt, with a liquid formulation of the material of formula I.

Sprayable solutions suitable for direct application contain e.g. mineral oil fractions of high to medium boiling range, particularly over 100° C, such as diesel oil or kerosene and furthermore coal tar oil or vegetable or animal oils, together with hydrocarbons such as alkylated naphthalene, tetrahydronaphthalene, xylene mixtures, cyclohexanols, and optionally in addition ketones, chlorinated hydrocarbons such as tetrachloroethane, trichloroethylene, or tri- and tetrachlorobenzenes.

For use in aqueous application forms, emulsion concentrates, pastes or wettable spraying powders are used with the addition of water. As emulsifiers or dispersants there can be used non-ionogenic products, e.g. condensation products of aliphatic alcohols, amines or carboxylic acids with a long chain hydrocarbon residue of from 10 to 30 carbon atoms with ethylene oxide, for example the condensation product of octadecyl alcohol and 25 to 30 mols ethyleneoxide, or that of soya fatty acid and 30 mols ethylene oxide or that of technical oleylamine and 15 mols ethyleneoxide or that of dodecylmercaptan and 12 mols ethyleneoxide. However condensation products of ethyleneoxide with hydroaromatic-polycyclic carboxylic acids and amines can also be used. Amongst anionic emulsifying agents which may be used there should be mentioned: the sodium salt of dodecylalcoholsulphonate esters, the sodium salt of dodecylbenzenesulfonic acid, the potassium or triethanolamine salt of oleic acid or of abietic acid or of mixtures of these acids, or the sodium salt of a petroleum sulphonic acid. As cationic dispersing agents, there can be used quaternary ammonium and phosphonium compounds, e.g. cetylpyridiniumchloride or dioxyethylbenzyldodecylammonium chloride. If the active substance of the invention is to be used in the form of a dusting or scattering preparation, then it can contain talcum, kaolin, bentonite, sand, calcium carbonate, calcium phosphate or even coal as solid carrier materials. Evaporating agents can also be added to the stored goods such as, for example, porous clay bars impregnated with the active agent. The various preparations can contain in customary fashion the addition of materials which improve the distribution, the adhesive strength, or the penetration depth; among such materials should be mentioned fatty acids, resins, glues, casein, or e.g. alginates. The use of preparations in granulated form is also very useful. The compound of the invention can be present as sole active material in the pest control agents, or it may be in combination with other insecticides or acaricides.

The following Examples will serve to illustrate the invention:

EXAMPLE 1

27.6 parts of the sodium salt of α-hydroxymethylene-propionic acid methyl-ester,

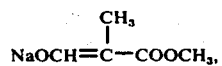

were warmed in 200 parts by volume of acetonitrile to 40° – 50° C. At this temperature, 33 parts of dimethyl-thiochlorophosphate were added dropwise and the mixture then maintained for 4 hours with stirring at 40°–50° C. After cooling, the salts were filtered off with suction and the solvent removed in vacuo at 50° C bath temperature. The residue was taken up in methylene chloride and rinsed with N caustic soda. After the evaporation of the solvent in vacuo, the active substance according to the invention of the formula

was obtained in the form of an oil.

The compound boiled at 80° – 90° C (0.01 mm Hg).

EXAMPLE 2

A. Dusting agent: Equal parts of the active agent according to the invention and precipitated silica were finely ground. By mixing with kaolin or talcum, it was possible to manufacture dusting agents with the preferred 1–6% content of active substance.

B. Powder for spraying: For the manufacture of a water soluble spraying powder, the following components were mixed and finely ground:
  50 parts active agent of formula I
  20 parts highly absorbent silica
  25 Bolus alba (Kaolin)
  1.5 parts sodium 1-benzyl-2-stearyl-benzimidazol-6,3′-disulphonate.

3.5 parts of a reaction product of p-tert, octylphenol and ethyleneoxide.

C. Emulsion concentrates: (a) 40 parts of the active substance of formula I were mixed with 10 parts of a mixture of an anionic surface active compound, preferably the calcium or magnesium salt of monolaurylbenzenemonosulphonic acid, and a nonionic surface active compound, preferably a polyethyleneglycolether of monosorbitollaureate, and the whole dissolved in a little xylene. The solution was then made up with xylene to 100 ml and a clear solution was thus obtained which could be used as a spraying agent concentrate and which gave a stable emulsion on being poured into water; (b) it was also possible to formulate an emulsion concentrate according to the following instruction:
  20 parts active agent
  70 parts xylene
  10 parts of a mixture of a reaction product of an alkylphenol with ethyleneoxide and calciumdodecylbenzenesulphonate were mixed together. On dilution with water to the desired concentration, a sprayable emulsion resulted.

D. Granulate: 7.5 grams of the active agent of the formula were dissolved in 100 ml acetone and the so obtained acetonic solution added to 92 grams of coarsely granulated attapulgite.

The whole was well mixed and the solvent was removed in a rotary evaporator. A granulate was obtained with 7.5% active substance content.

EXAMPLE 3

Gas Action against adult houseflies

Using a pipette 10 mg of active substance were placed on a watch glass which was then covered with a wire mesh and placed in a 2 liter glass cylinder. Immediately thereafter 30 houseflies were introduced into the container which was then sealed.

A comparative test between compound 1 and PHOSDRIN (Registered Trade Mark) carried out according to this method gave the following mortality periods in minutes for 10%, 50% and 100% kill of the test animals.

| Active substance | Mortality time for a percentage of the houseflies | | | Acute oral toxicity LD$_{50}$ (mg/kg) (rats) |
|---|---|---|---|---|
| | 10% | 50% | 100% | |
| Phosdrin (Registered Trade Mark) | 22′ | 25′ | 30′ | 3–7 |
| Compound I | 5′ | 6′ | 25′ | 500 |

EXAMPLE 4

Ingestion test with one day old houseflies (Musca domestica)

Dilution series were manufactured with water. As solvent for the test preparations and similarly as a nutrition agent for the flies, 30% sugar water was used which had been coloured with chlorantin light red (as an attractant). The dilutions were tested with one day old houseflies. The 1, 2 and 4 hour controls enabled the speed of action to be determined. By means of the 24 hour control the limit concentration (action strength) could also be determined.

| Active Substance Concentration in 30% sugar water | % flies killed with active agent | | | | | | | |
|---|---|---|---|---|---|---|---|---|
| | Phosdrin | | | | Compound 1 | | | |
| | after an exposure time (hours) | | | | | | | |
| ppm | 1 | 2 | 4 | 24 | 1 | 2 | 4 | 24 |
| 100 | 100 | 100 | 100 | 100 | 100 | 100 | 100 | 100 |
| 50 | 30 | 70 | 80 | 100 | 60 | 90 | 100 | 100 |
| 25 | 20 | 40 | 60 | 100 | 40 | 70 | 100 | 100 |
| 12 | 0 | 0 | 20 | 90 | 40 | 70 | 100 | 100 |
| 6 | 0 | 0 | 10 | 80 | 30 | 40 | 100 | 100 |
| 3 | 0 | 0 | 0 | 20 | 10 | 20 | 50 | 90 |
| 1.5 | 0 | 0 | 0 | 0 | 0 | 0 | 0 | 10 |
| 0.8 | 0 | 0 | 0 | 0 | 0 | 0 | 0 | 0 |
| 0.4 | 0 | 0 | 0 | 0 | 0 | 0 | 0 | 0 |

EXAMPLE 5

DURABILITY TEST BETWEEN DDVP AND COMPOUND 1 METHOD

Wheat was shaken up with 5% dusting agent and then mixed again repeatedly with untreated wheat at half the poison concentration. In this way, a dilution series with concentrations of 50 – 25 – 12 – 6 – 3 – 1.5 ppm was obtained. In order to allow the duration differences between DDVP and Compound 1 to be demonstrated even better, the containers filled with the treated wheat (sized for 500 grams of wheat) were stored unsealed.

Since the test is repeated once per month, the desired information is obtained concerning the residual effect. In the test, the important pests in storage protection were chosen, viz, the grain weevil (Sitophilus granarius) - lesser grain borer (Rhizopertha dominica) and the larvae of the Khapra beetle (Trogoderma granarium), which are very resistant to insecticides. 20 test insects were tested per concentration and the results are expressed in the following table.

EXAMPLE 6

DIFFUSION ACTION IN WHEAT

A plexiglass box was divided by means of wire grids into ten vertical layers each 1 cm thick. Each compartment was filled with wheat grains. The first compartment contained wheat grains which had been treated with 50 ppm active agent (5% dusting agent). The remainder of the compartment contained untreated wheat. All the compartments were then supplied with grain weevils. The mortality was noted after 7 days exposure time and the results are expressed in the following table. Diffusion of active substance in gas phase between the wheat grains

| | (Test Animal Sit. Granarius) | |
|---|---|---|
| Distance in cm from the treated wheat layer | Mortality in % after 7 days exposure time with | |
| | DDVP | Compound I |
| 1 | 100 | 100 |
| 2 | 100 | 100 |
| 3 | 80 | 100 |
| 4 | 0 | 100 |
| 5 | 0 | 90 |
| 6 | 0 | 15 |

We claim:

1. An insecticidal composition which comprises (1) as an active component an insecticidally effective amount of the compound of the formula

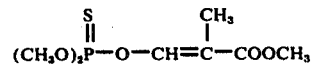

and (2) a suitable carrier.

2. The method of combatting insects which comprise applying thereto an insecticidally effective amount of the compound of the formula

* * * * *

Table 1

| | Disinfection test with DDVP and Compound 1 on Wheat | | | | | | | | | | | | | | | | | |
|---|---|---|---|---|---|---|---|---|---|---|---|---|---|---|---|---|---|---|
| DDVP (Dimethyldichlorvinylphosphate) | | | | | | | | | | | | | 20 test animals per concentration | | | | | |
| | % animals dead after one week exposure, at | | | | | | | | | | | | | | | | | |
| Treated Wheat Stored For | Sitophilus granarius | | | | | | Rhizopertha dominica | | | | | | Trogoderma granarium (L) | | | | | |
| | concentration of active substance in wheat (ppm) | | | | | | | | | | | | | | | | | |
| | 50 | 25 | 12 | 6 | 3 | 1.5 | 50 | 25 | 12 | 6 | 3 | 1.5 | 50 | 25 | 12 | 6 | 3 | 1.5 |
| fresh | 100 | 100 | 100 | 100 | 100 | 100 | 100 | 100 | 100 | 100 | 100 | 95 | 100 | 100 | 100 | 100 | 100 | 85 |
| 1 month | 100 | 100 | 100 | 25 | 5 | 0 | 100 | 65 | 15 | 10 | 5 | 0 | 100 | 75 | 5 | 0 | 0 | 0 |
| 2 months | 100 | 100 | 55 | 0 | 0 | 0 | 95 | 40 | 20 | 5 | 0 | 5 | 45 | 10 | 0 | 0 | 0 | 0 |
| 3 months | 99 | 50 | 0 | 0 | 0 | 0 | 80 | 15 | 0 | 0 | 0 | 0 | 0 | 0 | 0 | 0 | 0 | 0 |
| Compound 1 | | | | | | | | | | | | | | | | | | |
| fresh | 100 | 100 | 100 | 100 | 100 | 100 | 100 | 100 | 100 | 100 | 90 | 20 | 100 | 100 | 100 | 100 | 95 | 90 |
| 1 month | 100 | 100 | 100 | 100 | 100 | 90 | 100 | 100 | 85 | 60 | 5 | 0 | 100 | 100 | 95 | 85 | 10 | 0 |
| 2 months | 100 | 100 | 100 | 100 | 100 | 100 | 100 | 80 | 70 | 40 | 10 | 15 | 100 | 100 | 85 | 30 | 0 | 0 |
| 3 months | 100 | 100 | 100 | 100 | 95 | 70 | 100 | 75 | 35 | 15 | 15 | 0 | 100 | 100 | 55 | 10 | 0 | 0 |
| Control | | | | | | | | | | | | | | | | | | |
| fresh | 0 | | | | | | 0 | | | | | | 0 | | | | | |
| 1 month | 0 | | | | | | 0 | | | | | | 0 | | | | | |
| 2 months | 0 | | | | | | 5 | | | | | | 0 | | | | | |
| 3 months | 0 | | | | | | 0 | | | | | | 0 | | | | | |